United States Patent

Baudino

Patent Number: 5,865,843
Date of Patent: Feb. 2, 1999

[54] MEDICAL NEUROLOGICAL LEAD WITH INTEGRAL FIXATION MECHANISM

[75] Inventor: Michael David Baudino, Coon Rapids, Minn.

[73] Assignee: Medtronic Inc., Minneapolis, Minn.

[21] Appl. No.: 842,158

[22] Filed: Apr. 23, 1997

[51] Int. Cl.[6] .................................................. A61N 1/05
[52] U.S. Cl. .......................................... 607/116; 607/126
[58] Field of Search ............................ 600/375; 607/131, 607/132, 120, 126, 116; 604/27

[56] References Cited

U.S. PATENT DOCUMENTS 5,003,992  4/1991  Holleman et al. ....................... 607/127
5,058,584  10/1991  Bourgeois .
5,090,422  2/1992  Dahl et al. ............................. 600/375

*Primary Examiner*—Scott M. Getzow
*Attorney, Agent, or Firm*—Banner & Witcoff Ltd

[57] ABSTRACT

A medical, neurological lead includes structure preferably integral to the lead. A helical anchor is raised or channeled into the exterior of the lead. A companion helical valley extends alongside a helical protuberance. Both are created in the lead during the process of its formation, by suitable casting or extrusion or other techniques. Soft tissue and a fibrotic sheath form about the valley and protuberance of the lead such that the lead is fixed longitudinally and laterally, acutely and chronically, by the anchor. The pitch of the valley and protuberance relative to the longitudinal axis of the lead, and the smoothness of the exterior of the lead, are chosen such that the lead may, if and when necessary, be literally screwed from the body, by turn of the lead.

14 Claims, 1 Drawing Sheet

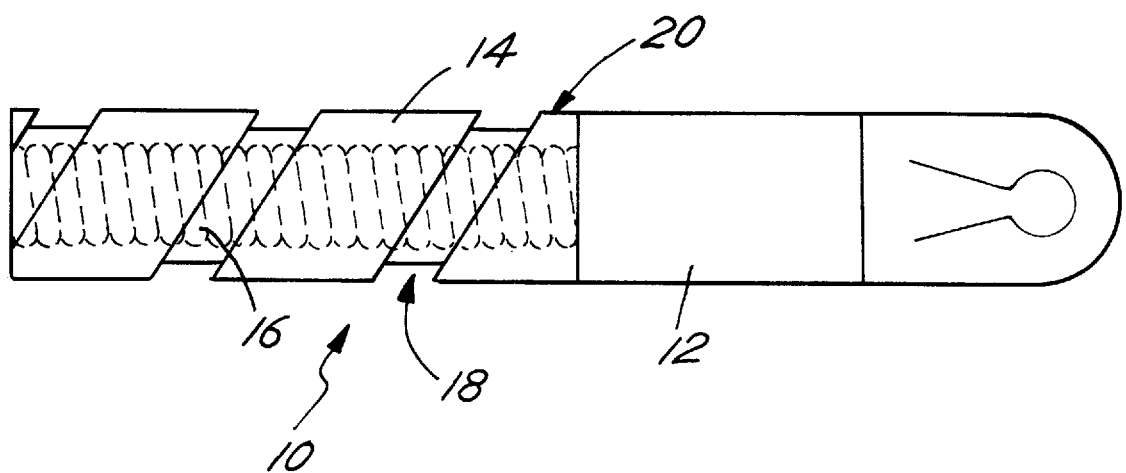
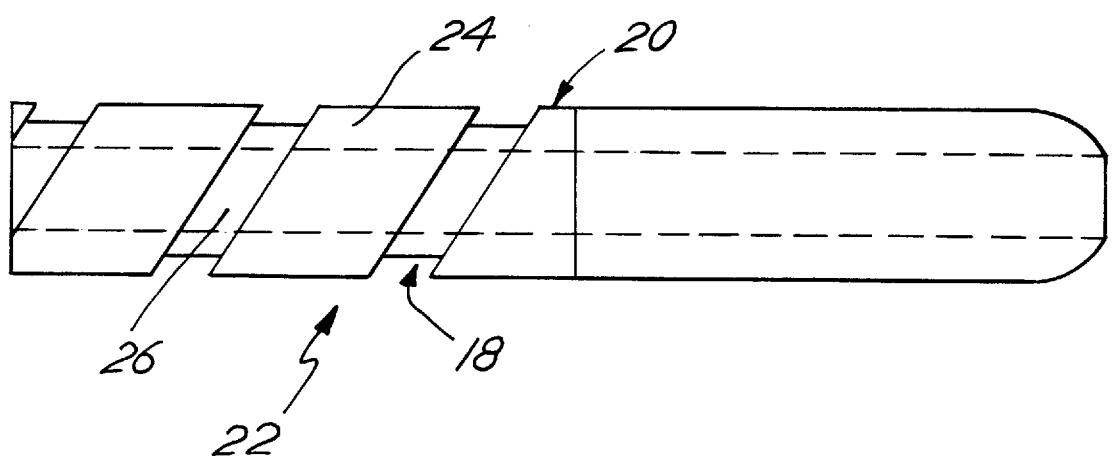

MEDICAL NEUROLOGICAL LEAD WITH INTEGRAL FIXATION MECHANISM

BACKGROUND OF THE INVENTION

This invention relates to medical, neurological leads of the type used for insertion into the human body, for transmission of therapeutic drugs and/or electrical signals to body organs such as the spinal cord or brain, for acute and chronic pain relief, acute and chronic treatment of disease, and the like. More specifically, this invention relates to the mechanisms and methods by which such leads are secured to the human body.

The field of the application of therapeutic drugs and electrical signals to bodily organs such as the spinal cord and brain is rapidly advancing. The assignee of the present invention, Medtronic, Inc. is a leader in the field. Scientists and engineers at Medtronic have created programmable, electronic, implantable devices which deliver drugs and/or electrical stimulation in programs of therapy for the benefit of mankind. Implantable electrical devices are now capable of relieving chronic, inoperable pain by interfering with the transmission of pain signals in the spinal cord and brain. Implantable drug delivery devices are capable of delivering pain relieving drugs to the same dramatic effect. Both types of devices are also capable of new therapies for treatment of a variety of diseases. An advantage of the electrical devices is that typically no drugs are necessary. With the drug delivery devices, an advantage is that drug dosages are reduced relative to other therapies because the drugs are delivered directly to desired locations of therapy, rather than in remote locations such as the blood vessels of the extremities, and without concern for bodily elimination or chemical interaction. New applications of electrical and drug delivery therapies to diseases and acute and chronic conditions are being discovered rapidly.

With the electrical devices, electrical stimulation is typically delivered from the devices to the body through wired leads, to electrodes. The electrodes are located on and exposed to the body on the distal extremity of the leads, and the leads typically extend into and along the epidural space of the spinal cord, or into the brain at surgically drilled boreholes. The leads may also be subcutaneous where necessary. As an example, leads may extend from devices implanted above the clavicles, under the skin, to a bore hole atop the skull, and thence deep into brain tissue. With the drug delivery devices, catheters, which for purposes of this description are also considered "leads," extend in similar ways. To date, as known to the inventor, leads in the described applications are typically smooth walled, plastic, tubular members, although variation is possible.

When surgery for implantation of neurological leads occurs and is completed, the human body reacts acutely in that soft tissues adjacent surgical openings close about the leads. Chronically, a fibrotic sheath develops. With smooth walled leads, neither the closed soft tissues nor the fibrotic sheaths are adherent to leads. As a consequence, neurological leads must generally be fixed to the body by sutures, or alternative anchors fastened to the leads and the human body.

U.S. Pat. No. 5,058,584, which illustrates an implantable electrical pulse or signal generator delivering bursts of high frequency stimulation to the epidural space of the spinal cord, is incorporated by reference.

SUMMARY OF THE INVENTION

An object of the present invention is to advance the art of medical, neurological leads, including electrical leads and catheters.

Another object is to advance the structures and techniques by which medical, neurological leads are fastened to the human body.

Yet another object of the invention is to provide a structure by which medical, neurological leads are fastened to the human body such that fixation to the body is long-lasting and stable, in the rostral/caudal or longitudinal direction, and laterally.

Still another object of the invention is to provide a structure as described which does not require complicated, surgical or even destructive techniques for removal.

These and other objects, and the advantages, of the present invention are best understood by a full reading of all parts of this specification in combination.

Briefly, in summary, the invention comprises structure preferably integral to a medical, neurological lead. As now contemplated and preferred, a medical, neurological lead is formed with a helical anchor raised or etched into the exterior of the lead. A helical valley extends alongside a helical protuberance. Both are created in the lead during the process of its formation, by suitable casting, etching, extrusion or other techniques. Soft tissue and a fibrotic sheath form about the lead's exterior helical valley and helical protuberance such that the lead is fixed longitudinally and laterally, acutely and chronically, by the anchor. The pitch of the valley and protuberance relative to the longitudinal axis of the lead, and the smoothness of the exterior of the lead, are chosen such that the lead may, if and when necessary, be literally screwed from the body, by turn of the lead.

For greater detail, a detailed description of the preferred embodiment follows this summary. The detailed description references the accompanying drawing. For rapid orientation to the drawing, a brief description of the drawing precedes the detailed description.

BRIEF DESCRIPTION OF THE DRAWING

The drawing of this specification consists of two figures, FIG. 1 and FIG. 2, which diagrammatically represent a distal portion of the preferred medical, neurological, electrical lead of the invention, and a distal portion of the preferred medical, neurological drug deliver catheter or lead of the invention.

For ease of reference, the numerals used in the drawing are listed as follows:
10 a distal portion 10 of the lead of FIG. 1
12 an electrode 12 on the lead 10
14 a lead sheath or body 14
16 an internal core 16
18 a helical groove 18
20 a helical land 20
22 a distal portion of the lead of FIG. 2
24 lead body 24
26 passage 26

DETAILED DESCRIPTION OF THE PREFERRED EMBODIMENTS

Referring to FIGS. 1 and 2 of the accompany drawing, a preferred lead of the invention includes a distal portion 10, and associated central and proximal portions not shown. As known to persons of ordinary skill in the art, if electrical, the lead may connect to an electrical signal generating device (hereafter "a signal generator") which may or may not be implantable in whole or in part into the human body. If the lead is a drug delivery lead, the lead may connect to a drug pump, which also may or may not be implantable. In either case, the lead is intended to have at least a portion engaged in the tissue of the body. Depending on the application, the lead may engage tissue in the proximal, central, or distal portions of the lead. The lead may or may not enter the epidural space which surrounds the spinal cord, or the lead may enter the brain through the skull. Generally, the lead is substantially elongated, with the dimension of its length one hundred or more times the dimension of its width.

Again if electrical, as in FIG. 1, the lead 10 may include one or more electrodes, such as an electrode designated 12. The electrode may be annular, surrounding the lead body, or in other shape or form. If a drug delivery lead, as in FIG. 2, the lead 22 may include one or more openings for transmission of drugs from the drug pump to the body, in the place of electrodes, or in addition to electrodes.

The lead 10 or 22 is desirably, generally circular in cross-section, although variations are within contemplation. Focusing on an electrical lead of FIG. 1, for illustration, an insulating, annular, external lead sheath or body 14 surrounds an electrically transmissive internal core 16, shown in phantom. The core 16 frequently takes the form of a helically wound or coiled wire, interconnected to the distal electrode(s) and the proximal signal generator. The wire has a direction of its winding, which is right hand or left hand, clockwise or counterclockwise. As desired, although not presently contemplated, the lead may also include additional intermediate or other layers, or other components.

As exemplified by a helical groove 18, a helical valley and companion helical protuberance exist on the outermost, circumferential surface of the lead. As most highly preferred, the groove 18 is laser etched on the lead, substantially completely throughout its operative length, from adjacent the distal electrodes or other distal structure, through its central portion and to its proximal portion. Alternate techniques for creation of the groove 18 are contemplated, including casting, chemical etching, extrusion, or other techniques. Also as most highly preferred, the groove 18 is continuous, and has a depth of from about one-one thousandths of an inch to about five one thousandths of an inch. Consistently, the width of the groove 18 is from about ten thousandths of an inch to twenty thousandths of an inch. The groove 18 may be formed in one helix as shown, or in multiple helixes alongside each other.

As a part of being helical, the groove 18 and associated helical "land" 20 (constituting a protuberance as described) have a helical pitch relative to the longitudinal extent and axis of the lead. The pitch is desirably although not necessarily opposite the pitch of the coil or core 16, and the pitch is most preferably in a range within the limits of from about zero degrees (no pitch) to about ninety degrees (infinite pitch) in which manual forces generated by spinning the lead are effective to rotate the lead in situ and cause the lead to move longitudinally relative to any surrounding soft tissue and/or fibrotic sheath. The surface finish of the exterior of the lead in the area of the groove and land, at least to the extent to which contact with tissue is anticipated, is sufficiently smooth that ingrowth of tissue preferably does not occur, and after acute and/or chronic implantation, the lead may be helically advanced and/or retracted relative to adjacent bodily tissue.

Focusing on the drug deliver lead or catheter of FIG. 2, for illustration, a liquid insulating, annular, external lead sheath or body 24 surrounds a liquid transmissive internal and open core or passage 26, shown in phantom.

As can now be anticipated, implantation of the lead in the human body, and chronic removability, are contemplated. As preferred, any appropriate neurological procedure is begun, and the lead introduced to the body. For purposes of illustration, assume introduction to the epidural space. The opening to the epidural space is maintained, as for example by an introducer, while the location of the lead is maximized. By fluoroscan or other technique, the location of the lead is visualized, and by immediate or following acute procedures, effectiveness is optimized. The tissue of the body adjacent the epidural space is allowed to close about the lead body, and allowed to heal, thereby forming a fibrotic sheath. Due to the smooth finish of the lead body, the tissue/lead body interface develops such that the lead body may be manually spiraled relative to the body, perhaps after some initial inertia, but is otherwise generally immobile. For so long as therapy is effective and also not harmful, the lead is maintained in place.

Yet, whenever conditions are such that lead movement is required, as when lead removal is desired, the lead may be manually gripped and rotated such that the lead is helically spun and moved longitudinally. With a lead as contemplated, with one or more continuous helical valleys and protuberances from the are of introduction to the body to the distal end, the lead may be completely spun from the body. To assure removal of the lead electrode, or electrode array, if any, and the lead tip, all distal structure of the lead adjacent the protuberance is most preferably sized in diameter to be equal to or less than the diameter of the lead valley.

For all purposes of electrical stimulation and/or drug delivery, provision of the invented structure on a lead is "transparent," i.e., not adversely affective of function or structure.

The invention and the preferred embodiment of the invention are now described in such full, clear and concise terms as to enable a person or ordinary skill in the art to make and use the same without undue experimentation. Variations on and embellishments of the invented structure are no doubt possible. Therefore, to particularly point and distinctly claim the subjects regarded as invention, the following claims conclude this specification. Interpretation of the claims according to long-standing principles of interpretation, and a range of equivalents, are anticipated.

What is claimed is:

1. A medical, neurological lead for such use as electrical signal and/or drug delivery comprising:

an elongated body with a distal portion, a central portion and a proximal portion, said body including delivery means extending to said distal portion;

an external, helical anchor created by grooves on said body, said grooves extending from said proximal portion to said central portion of said body; and a non-porous exterior surface extending from said central portion to said distal portion of said body.

2. A medical, neurological lead for such use as electrical signal delivery comprising:

an elongated body with a distal portion, a central portion and a proximal portion, said body including electrical signal delivery means extending to said distal portion;

an external, helical anchor created by helical valleys and companion protuberances on said body, said helical valleys and companion protuberances extending from said proximal portion to said central portion of said body; and a non-porous exterior surface extending from said central portion to said distal portion of said body.

3. The medical, neurological, electrical signal delivery lead as in claim 2, wherein said electrical signal delivery means is an implantable lead having at least one electrode.

4. The medical, neurological, electrical signal delivery lead as in claim 2, wherein said helical valley is a groove and said protuberance being a land.

5. The medical, neurological, electrical signal delivery lead as in claim 2, wherein said helical anchor includes a single helical valley and a single, companion helical protuberance.

6. The medical, neurological, electrical signal delivery lead as in claim 2, wherein said helical anchor extends substantially throughout said central portion of said lead to said distal portion.

7. The medical, neurological, electrical signal delivery lead as in claim 2, said lead including at least one electrode and said anchor extending to adjacent said electrode.

8. The medical, neurological lead as in claim 2, wherein a surface of said exterior of said lead and anchor being smooth as to tissue ingrowth.

9. A medical, neurological lead for such use as drug delivery comprising:

an elongated body with a distal portion, a central portion and a proximal portion, said body including drug delivery means extended to said distal portion; and an external, helical anchor created by helical valleys and companion protuberances on said body, said helical valleys and protuberances extending from said proximal portion to said central portion of said body.

10. The medical, neurological, drug delivery lead as in claim 9, wherein said drug delivery means is a catheter.

11. A method for inserting a medical, neurological lead into a human body, said lead having helical grooves created by helical valleys and companion protuberances on an outermost circumferential surface of said lead, comprising the steps of:

a) engaging body tissue by said lead;

b) helically advancing said lead by moving said lead in a substantially longitudinal direction relative to any surrounding soft said body tissue to position said lead; and c) forming a fibrotic sheath around said lead by allowing said body tissue to close and heal around said lead whereby said lead is anchored in place.

12. The method of claim 11 further comprising the steps of:

d) connecting said lead to a drug delivery means for dispensing therapeutic drugs to body organs through an internal and open core of said lead to said body tissue.

13. The method of claim 11 further comprising the step of:

d) connecting said lead to an electrical signal delivery means for providing electrical stimulation to said body tissue.

14. The method of claim 11, 12 or 13 further comprising the step of:

e) retracting said lead by gripping and rotating said lead such that said lead is helically spun and moved substantially longitudinally out of said body tissue.

* * * * *